United States Patent
Canady et al.

(10) Patent No.: US 11,253,310 B2
(45) Date of Patent: Feb. 22, 2022

(54) GAS-ENHANCED ELECTROSURGICAL GENERATOR

(71) Applicant: U.S. Patent Innovations, LLC, Takoma Park, MD (US)

(72) Inventors: Jerome Canady, Lakeland, FL (US); Taisen Zhuang, Vienna, VA (US); Shruti Wigh, Silver Spring, MD (US); Daniel Tabatabai, Annandale, VA (US)

(73) Assignee: U.S. Patent Innovations, LLC, Takoma Park, MD (US)

( * ) Notice: Subject to any disclaimer, the term of this patent is extended or adjusted under 35 U.S.C. 154(b) by 0 days.

(21) Appl. No.: 16/604,412

(22) PCT Filed: Apr. 10, 2018

(86) PCT No.: PCT/US2018/026894
§ 371 (c)(1),
(2) Date: Oct. 10, 2019

(87) PCT Pub. No.: WO2019/199281
PCT Pub. Date: Oct. 17, 2019

(65) Prior Publication Data
US 2021/0128222 A1    May 6, 2021

(51) Int. Cl.
*A61B 18/12* (2006.01)
*A61B 18/00* (2006.01)

(52) U.S. Cl.
CPC .... *A61B 18/1206* (2013.01); *A61B 2018/00017* (2013.01); *A61B 2018/00178* (2013.01);
(Continued)

(58) Field of Classification Search
CPC .............. A61B 18/1206; A61B 18/128; A61B 2018/00017; A61B 2018/00494; A61B 2018/00178; A61B 2018/00589
See application file for complete search history.

(56) References Cited

U.S. PATENT DOCUMENTS

| 4,040,426 A | 8/1977 | Morrison |
| 4,429,694 A | 2/1984 | McGreevy |

(Continued)

OTHER PUBLICATIONS

J. Elliott, et al., "Review of fluorescence guided surgery visualization and overlay techniques," Biomedical Optics Express 3765 (2015).

(Continued)

*Primary Examiner* — Daniel W Fowler
(74) *Attorney, Agent, or Firm* — 24IP Law Group USA, PLLC; Timothy Dewitt

(57) ABSTRACT

A gas-enhanced electrosurgical generator. The gas-enhanced generator has a housing, a first gas control module in the housing and configured to control flow of a first gas, a second gas control module in the housing and configured to control flow of a second gas, a high frequency power module, and a controller, processor or CPU within the housing and configured to control the first gas control module, the second gas control module and the high frequency power module. The first gas and second gas may be any of $CO_2$, argon and helium or another gas. The gas-enhanced electrosurgical generator may have a third gas control module in the housing and configured to control flow of a third gas and a third connector secured on an exterior of the housing.

11 Claims, 17 Drawing Sheets

(52) U.S. Cl.
CPC ............... *A61B 2018/00494* (2013.01); *A61B 2018/00589* (2013.01); *A61B 2018/128* (2013.01); *A61B 2560/0487* (2013.01); *A61B 2562/0247* (2013.01)

(56) References Cited

U.S. PATENT DOCUMENTS

| | | | |
|---|---|---|---|
| 4,635,735 A | | 1/1987 | Crownover |
| 4,781,175 A | | 11/1988 | McGreevy et al. |
| 5,207,675 A | | 5/1993 | Canady |
| 5,217,457 A | * | 6/1993 | Delahuerga ............ A61B 18/042 606/37 |
| 5,330,469 A | | 7/1994 | Fleenor |
| 5,342,349 A | * | 8/1994 | Kaufman ................. A61B 18/00 604/35 |
| 5,720,745 A | | 2/1998 | Farin et al. |
| 6,536,431 B1 | | 3/2003 | Simler |
| 2001/0002000 A1 | | 5/2001 | Kumar |
| 2002/0185127 A1 | | 12/2002 | Melker et al. |
| 2003/0144654 A1 | | 7/2003 | Hilal |
| 2005/0081541 A1 | * | 4/2005 | Copping ................... F25B 9/02 62/177 |
| 2005/0234326 A1 | * | 10/2005 | Uchikubo ............... A61B 90/36 600/407 |
| 2006/0095032 A1 | * | 5/2006 | Jackson ................ A61B 5/4233 606/41 |
| 2006/0106281 A1 | * | 5/2006 | Boulais ............... A61B 1/00105 600/104 |
| 2007/0083150 A1 | | 4/2007 | Nazarifar et al. |
| 2009/0088735 A1 | * | 4/2009 | Abboud ................. A61B 18/02 606/22 |
| 2010/0106080 A1 | | 4/2010 | Uesugi et al. |
| 2013/0296846 A1 | | 11/2013 | Canady et al. |
| 2014/0005665 A1 | | 1/2014 | Konesky et al. |
| 2014/0276682 A1 | * | 9/2014 | Hendrick ................ A61M 1/84 606/7 |
| 2014/0378892 A1 | | 12/2014 | Keidar et al. |
| 2015/0105765 A1 | * | 4/2015 | Panescu ................ A61B 18/02 606/34 |
| 2015/0238248 A1 | | 8/2015 | Thompson et al. |
| 2015/0342663 A1 | | 12/2015 | Canady et al. |
| 2016/0095644 A1 | | 4/2016 | Canady et al. |
| 2016/0235462 A1 | | 8/2016 | Canady et al. |
| 2016/0287824 A1 | | 10/2016 | Chang |
| 2017/0312003 A1 | | 11/2017 | Canady et al. |

OTHER PUBLICATIONS

K.Tipirneni, et al., "Oncologic Procedures Amenable to Fluorescence-guided Surgery," Annals of Surgery, Vo. 266, No. 1, Jul. 2017).

\* cited by examiner

GAS-ENHANCED ELECTROSURGICAL GENERATOR

CROSS-REFERENCE TO RELATED APPLICATIONS

None.

STATEMENT REGARDING FEDERALLY SPONSORED RESEARCH OR DEVELOPMENT

None.

BACKGROUND OF THE INVENTION

Field of the Invention

The present invention relates to gas-enhanced electrosurgical systems, and more particularly, to a gas control module for a gas-enhanced electrosurgical system.

Brief Description of the Related Art

A variety of different electrosurgical generators are known. U.S. Pat. No. 4,429,694 to McGreevy disclosed an electrosurgical generator and argon plasma system and a variety of different electrosurgical effects that can be achieved depending primarily on the characteristics of the electrical energy delivered from the electrosurgical generator. The electrosurgical effects included pure cutting effect, a combined cutting and hemostasis effect, a fulguration effect and a desiccation effect. Fulguration and desiccation sometimes are referred to collectively as coagulation.

Another method of monopolar electrosurgery via argon plasma technology was described by Morrison in U.S. Pat. No. 4,040,426 in 1977 and McGreevy U.S. Pat. No. 4,781,175. This method, referred to as argon plasma coagulation (APC) or argon beam coagulation is a non-contact monopolar thermoablative method of electrocoagulation that has been widely used in surgery for the last twenty years. In general, APC involves supplying an ionizable gas such as argon past the active electrode to target tissue and conducting electrical energy to the target tissue in ionized pathways as non-arcing diffuse current. Canady described in U.S. Pat. No. 5,207,675 the development of APC via a flexible catheter that allowed the use of APC in endoscopy. These new methods allowed the surgeon, endoscopist to combine standard monopolar electrocautery with a plasma gas for coagulation of tissue.

Yet another system is disclosed in U.S. Patent Application Publication No. 2013/0296846, which disclosed a system for simultaneously cutting and coagulating tissue. Another system, referred to as a "cold atmospheric plasma" system, is disclosed in U.S. Patent Application Publication No. 2014/0378892.

SUMMARY OF THE INVENTION

In a preferred embodiment, the present invention is a gas-enhanced electrosurgical generator. The gas-enhanced generator has a housing, a first gas control module in the housing and configured to control flow of a first gas, a second gas control module in the housing and configured to control flow of a second gas, a high frequency power module, and a controller, processor or CPU within the housing and configured to control the first gas control module, the second gas control module and the high frequency power module. The gas-enhanced electrosurgical generator further may have a first connector secured on an exterior of the housing, wherein the first connector comprises a fluid connector connected to an output port of the first gas control module, and a second connector secured on an exterior of the housing, wherein the second connector comprises a fluid connector connected to an output port of the second gas control module and an electrical connector connected to an output of the high frequency power module. The first gas and second gas may be any of $CO_2$, argon and helium or another gas. The gas-enhanced electrosurgical generator may have a third gas control module in the housing and configured to control flow of a third gas and a third connector secured on an exterior of the housing, wherein the third connector comprises a fluid connector connected to an output port of the third gas control module, and an electrical connector connected to an output of the high frequency power module. For example, the first gas comprises $CO_2$, the second gas comprises argon and the third gas comprises helium.

A gas-enhanced electrosurgical generator further may have a sub-system for controlling intraabdominal pressure in a patient. The sub-system for controlling intraabdominal pressure in a patient may have a 3-way proportional valve connected to an output port of the first gas control module, a pressure control valve having an internal pressure chamber, a port to the internal pressure chamber, an exhaust and an exterior port configured to release intraabdominal pressure from a patient, a first pressure sensor for sensing a pressure in the chamber, and a second pressure sensor connected to the exterior port. The gas-enhanced electrosurgical generator further may have a touch-screen display mounted to the housing. The generator further may have a graphical user interface, wherein the CPU is configured to control the graphical user interface and the touch-screen display.

In the gas-enhanced electrosurgical generator the HF power supply may be configured to supply high frequency energy to argon plasma coagulation attachment and supply low frequency electrosurgical energy to cold atmospheric plasma attachment based upon settings input through the touch screen.

The first, second and third gas control module each may have the following structure. The gas control module has an inlet port, a first solenoid valve connected to the inlet port, the first solenoid valve being configured to turn a flow of gas into the gas control module on and off, a first pressure sensor configured to sense a first pressure of gas entering the gas control module through the first solenoid valve, a first pressure regulator configured to change the first pressure of gas entering the first pressure regulator to a second pressure, a first flow sensor configured to sense a flow rate of gas exiting the first pressure regulator, a first proportional valve having an inlet and an outlet, the first proportional valve being configured to adjust the outlet as a percentage of the inlet, a second flow sensor configured to sense a flow of gas exiting the first proportional valve, a second solenoid valve being a 3-way valve, a vent connected to the second solenoid valve, a second pressure sensor for sensing a pressure of gas passing through the second solenoid valve, and a third solenoid valve, the third solenoid valve being configured to turn a flow of gas out of the gas control module on and off, and an exit port. The second pressure may lower than the first pressure and the first pressure regulator reduces the first pressure to the second pressure. The first pressure, for example, may be 50-100 psi and the second pressure may be 15-20 psi. The gas control module for a gas-enhanced electrosurgical system according to claim 1 may further have tubing for connecting the exit port to an electrosurgical accessory. The gas control module further comprising a support structure for supporting at least two of the first solenoid valve, the first pressure sensor, the first pressure regulator, the first flow sensor, the second solenoid valve, the second flow sensor, the second solenoid valve, the second pressure sensor and the third solenoid valve. The support structure may comprise a frame, a housing or another support element and, for example, may be formed of steel, plastic or a combination of those.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

BRIEF DESCRIPTION OF THE DRAWINGS

For a more complete understanding of the present invention and the advantages thereof, reference is now made to the following description and the accompanying drawings, in which.

DETAILED DESCRIPTION OF THE PREFERRED EMBODIMENTS

Figure 1A:
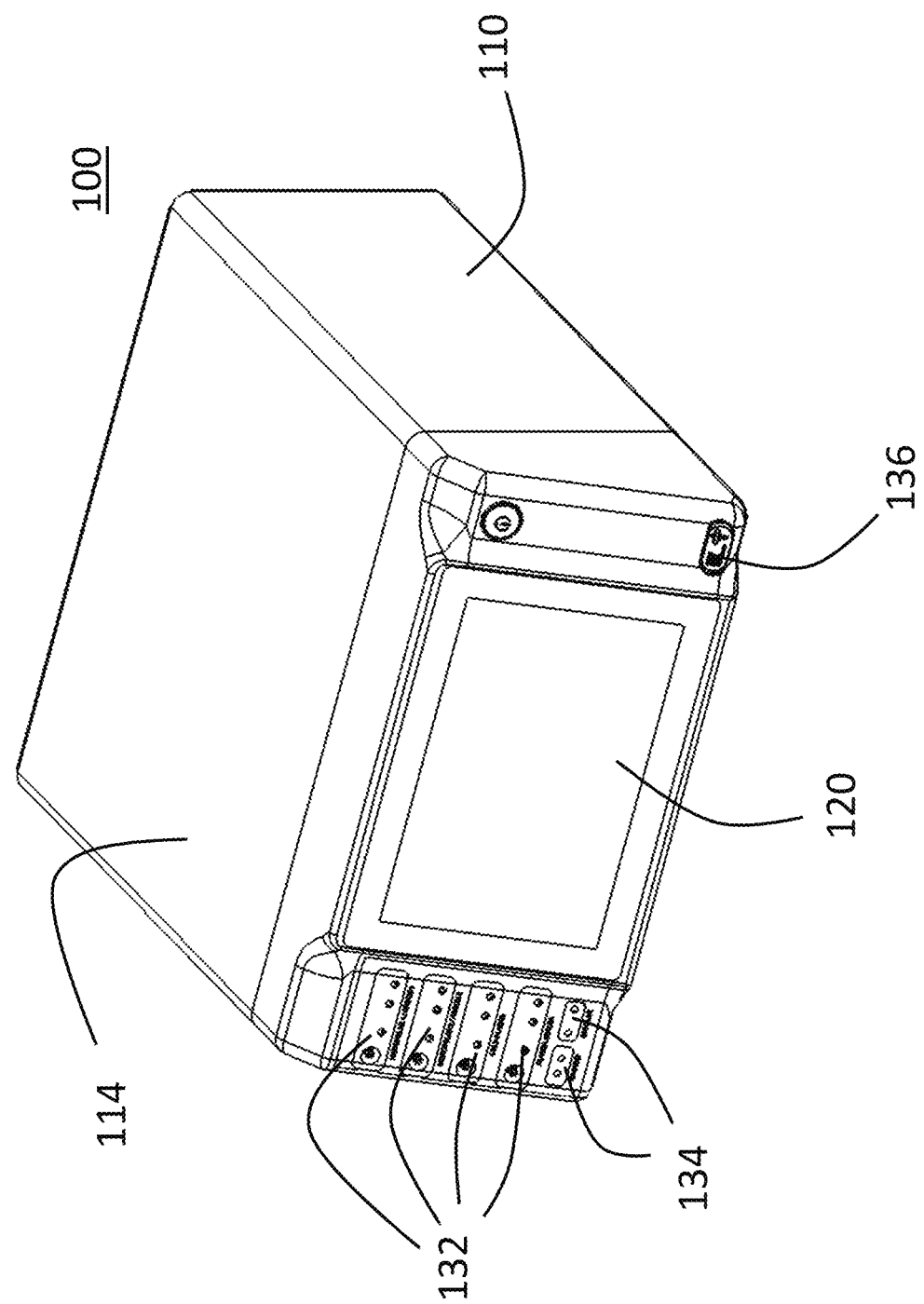
FIG. 1A is a perspective view of a preferred embodiment of a gas-enhanced electrosurgical generator.
Figure 1B:
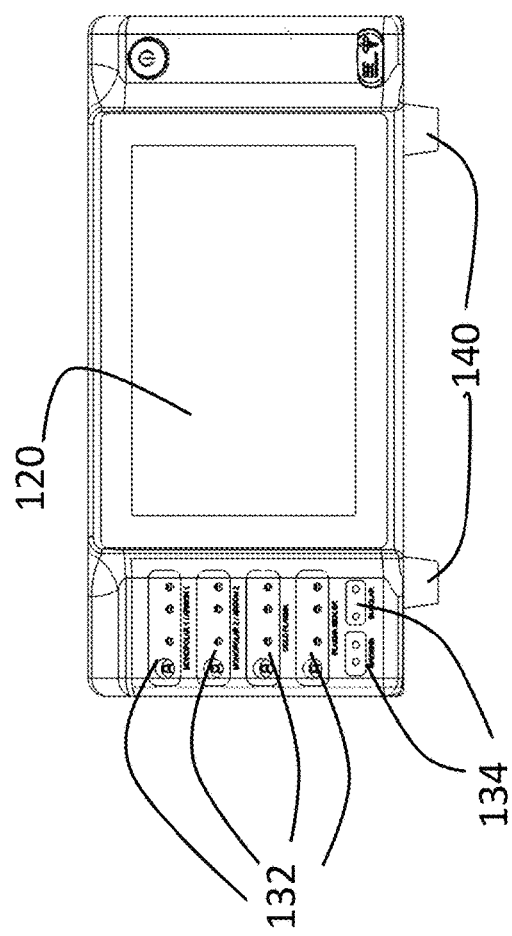
FIG. 1B is a front view of a preferred embodiment of a gas-enhanced electrosurgical generator.
Figure 1C:
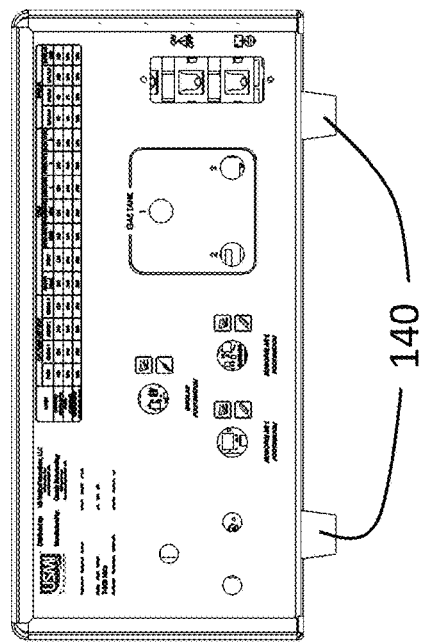
FIG. 1C is a rear view of a preferred embodiment of a gas-enhanced electrosurgical generator.
Figure 1D:
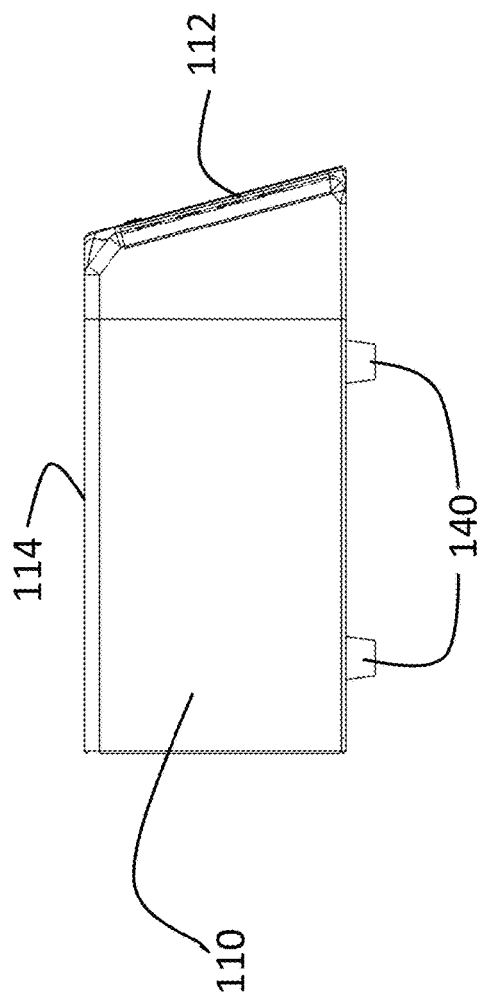
FIG. 1D is a left side view of a preferred embodiment of a gas-enhanced electrosurgical generator.
Figure 1E:
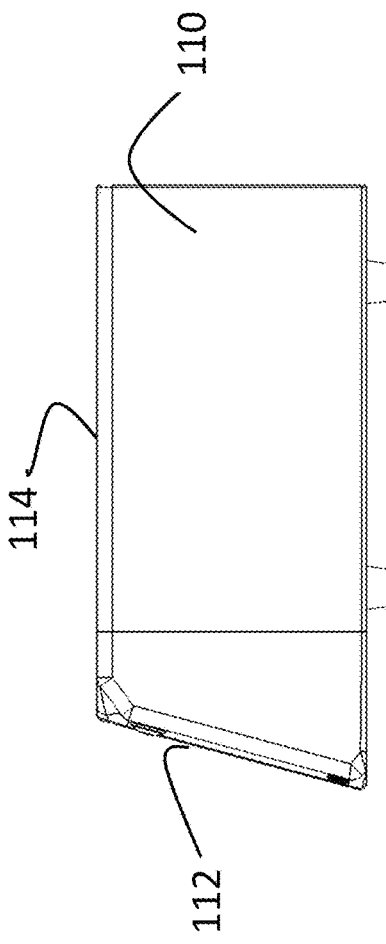
FIG. 1E is a right view of a preferred embodiment of a gas-enhanced electrosurgical generator.
Figure 1G:
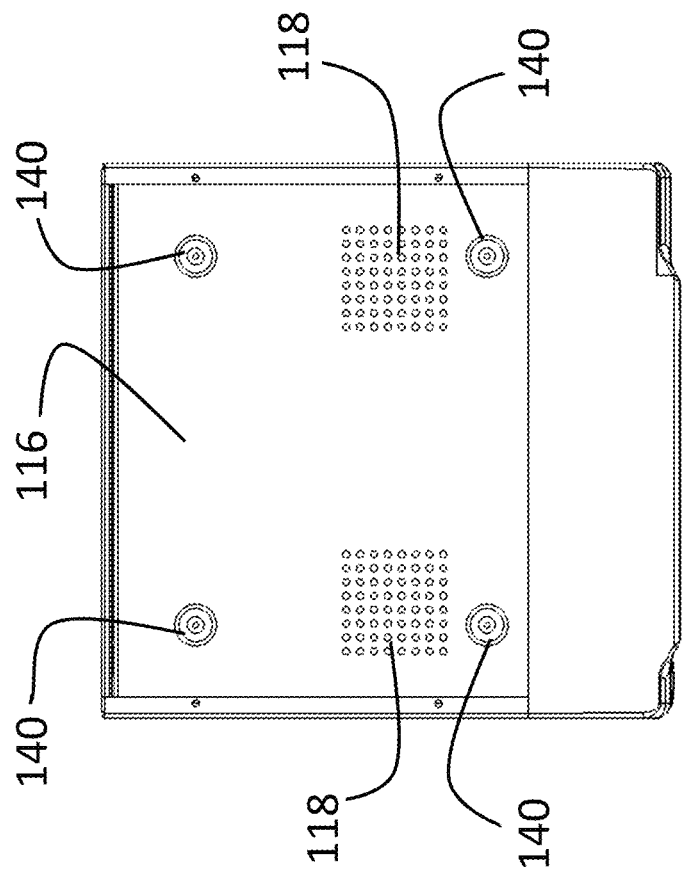
FIG. 1G is a bottom view of a preferred embodiment of a gas-enhanced electrosurgical generator.
Figure 1F:
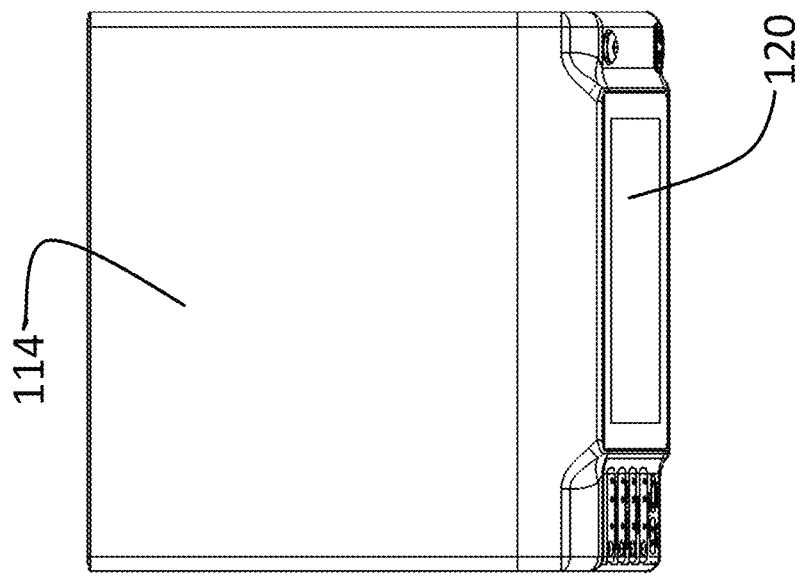
FIG. 1F is a top view of a preferred embodiment of a gas-enhanced electrosurgical generator.

The preferred embodiments of the inventions are described with reference to the drawings. A gas-enhanced electrosurgical generator 100 in accordance with a preferred embodiment of the present invention is shown in FIGS. 1A-1G. The gas-enhanced generator has a housing 110 made of a sturdy material such as plastic or metal similar to materials used for housings of conventional electrosurgical generators. The housing 110 has a removable cover 114. The housing 110 and cover 114 have means, such as screws 119, tongue and groove, or other structure for removably securing the cover to the housing. The cover 114 may comprise just the top of the housing or multiple sides, such as the top, right side and left side, of the housing 110. The housing 110 may have a plurality of feet or legs 140 attached to the bottom of the housing. The bottom 116 of the housing 110 may have a plurality of vents 118 for venting from the interior of the gas-enhanced generator.

On the face 112 of the housing 114 there is a touch-screen display 120 and a plurality of connectors 132, 134 for connecting various accessories to the generator, such as an argon plasma probe, a hybrid plasma probe, a cold atmospheric plasma probe, or any other electrosurgical attachment. There is a gas connector 136 for connecting, for example, a $CO_2$ supply for insufflating an abdomen. The face 112 of the housing 110 is at an angle other than 90 degrees with respect to the top and bottom of the housing 110 to provide for easier viewing and use of the touch screen display 120 by a user.

Figure 2A:
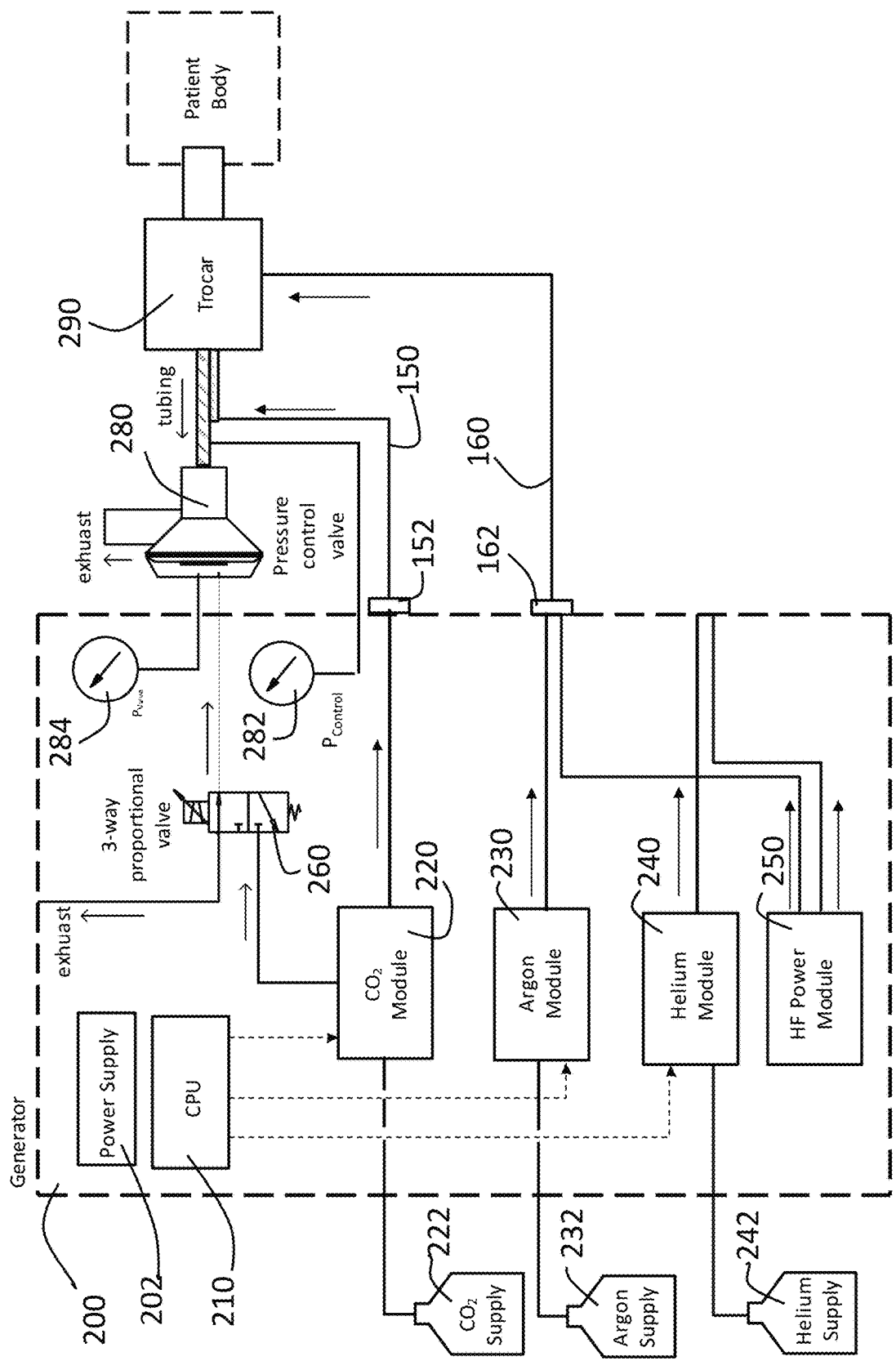
FIG. 2A is a block diagram of a preferred embodiment of a gas-enhanced electrosurgical generator having a pressure control system in accordance with the present invention configured to perform an argon-enhanced electrosurgical procedure.

One or more of the gas control modules may be mounting within a gas-enhanced electrosurgical generator 100. A gas pressure control system 200 for controlling a plurality of gas control modules 220, 230, 240 within a gas-enhanced electrosurgical generator is described with reference to FIGS. 2A-2D. A plurality of gas supplies 222, 232, 242 are connected to the gas pressure control system 200, and more specifically, to the respective gas control modules 220, 230, 240 within the gas pressure control system 200. The gas pressure control system 200 has a power supply 202 for supplying power to the various components of the system. A CPU 210 controls the gas pressure control modules 220, 230, 240 in accordance with settings or instructions entered into the system through a graphical user interface on the display 120. The system is shown with gas control modules for $CO_2$, argon and helium, but the system is not limited to those particular gases. In the embodiment shown in FIGS. 2A-2D, the $CO_2$ is shown as the gas used to insufflate an abdomen (or other area of a patient). The gas pressure control system 200 has a 3-way proportional valve connected to the gas control module 220. While FIG. 2A shows the 3-way proportional valve connected only to the CO2 control module 220, the 3-way proportional valves could be connected to a different gas control module 230 or 240. The gas pressure control system 200 further has an HF power module 250 for supplying high frequency electrical energy for various types of electrosurgical procedures. The HF power module contains conventional electronics such as are known for provide HF power in electrosurgical generators. Exemplary systems include, but are not limited to, those disclosed in U.S. Pat. Nos. 4,040,426 and 4,781,175. The system further could have a converter unit for converting the HF power to a lower frequency, such as may be used for cold atmospheric plasma and is described in U.S. Patent Application Publication No. 2015/0342663.

Figure 2B:
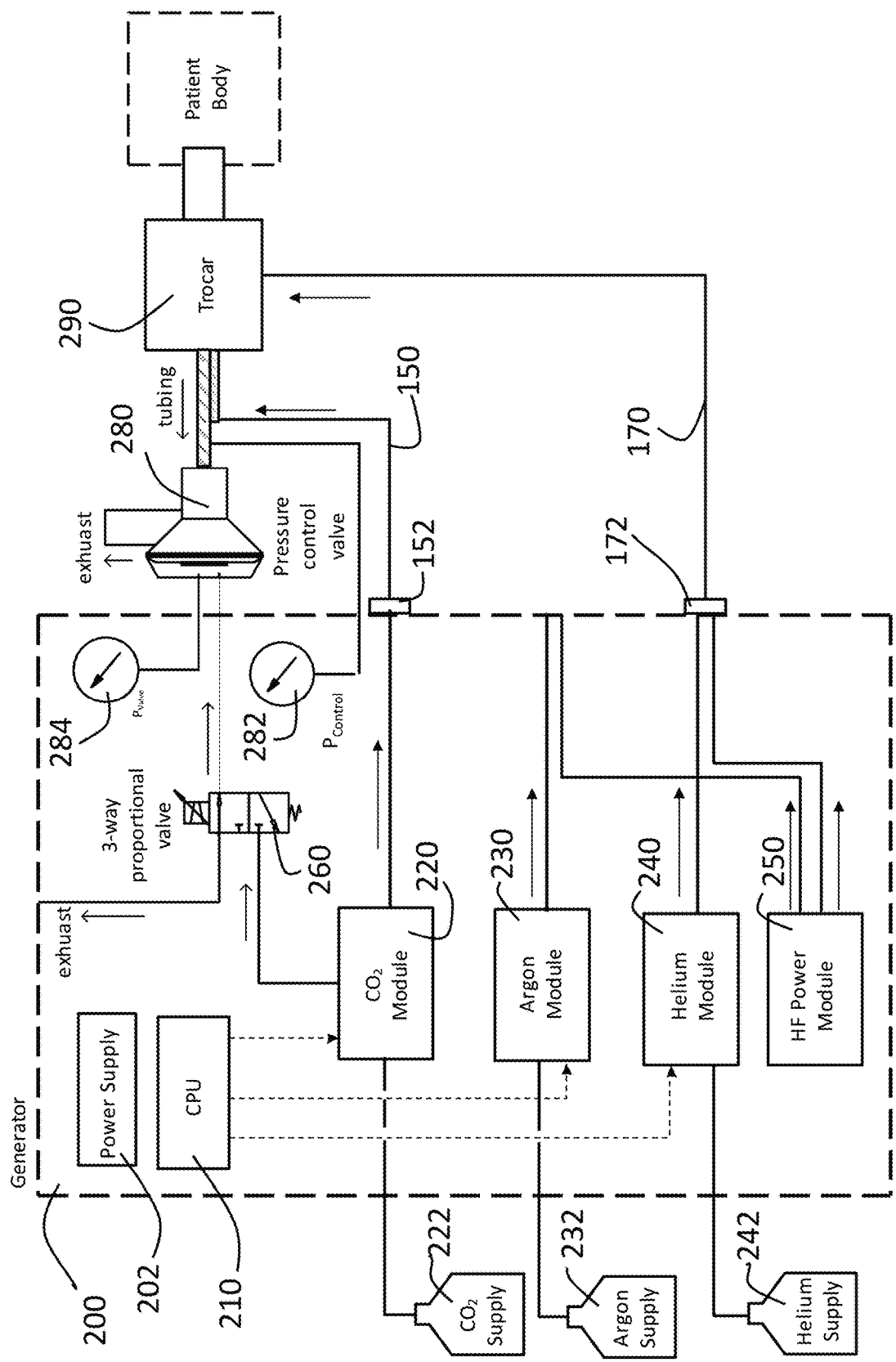
FIG. 2B is a block diagram of a preferred embodiment of a gas-enhanced electrosurgical generator having a pressure control system in accordance with the present invention configured to perform a cold atmospheric plasma procedure.
Figure 2C:
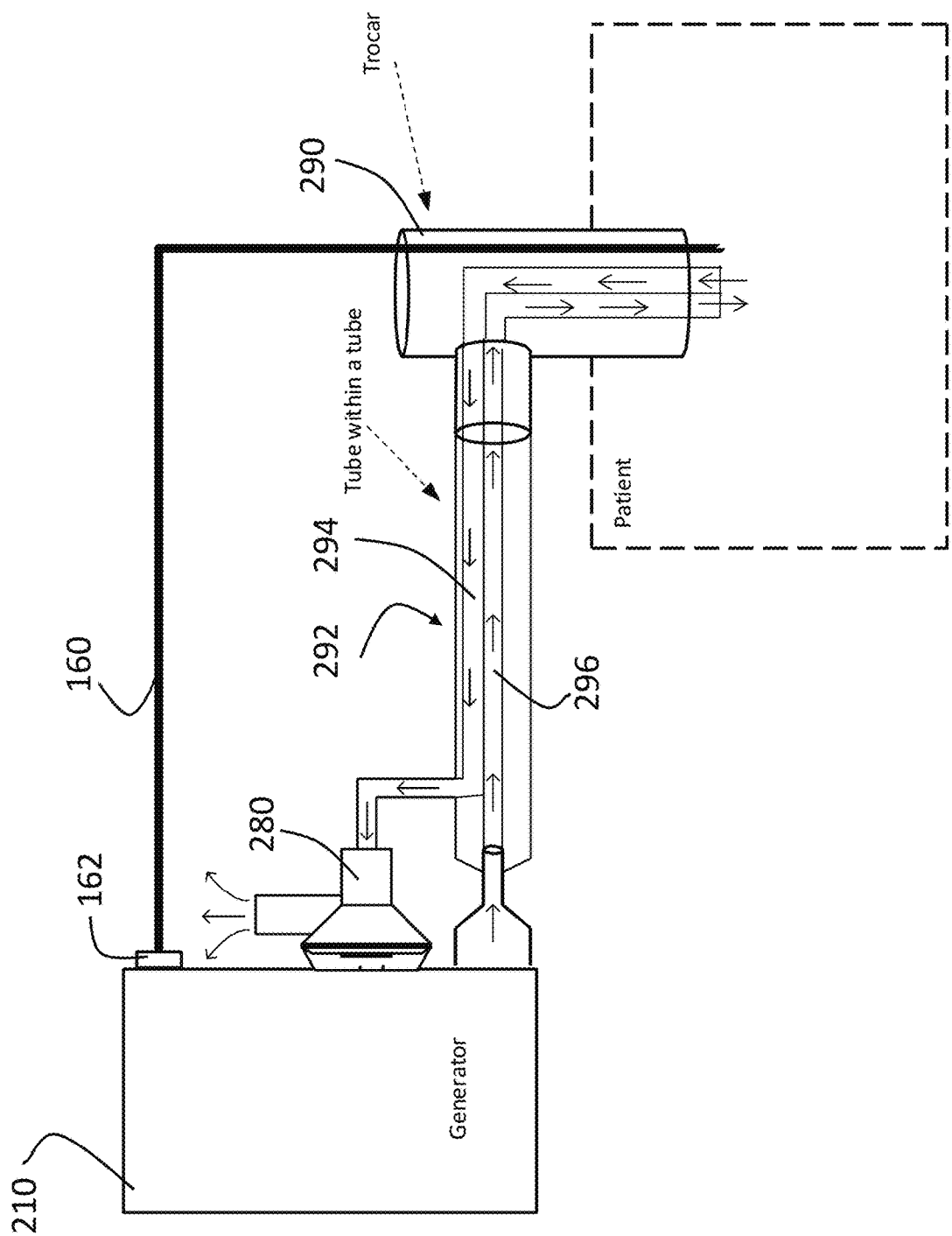
FIG. 2C is a diagram of a trocar for the embodiment of FIG. 2A in accordance with the present invention.

The outlet port of gas control module 220 is connected to a connector 136 on the generator housing. While connector 136 and the other connectors are shown on the front face of the housing 110, they could be elsewhere on the housing. The outlet ports of gas control modules 230, 240 each are connected to tubing or other channel to a connector 132. A connector 152 connects to connector 136 and is as tubing that runs to and connects to tubing 292. The tubing 292 is connected to a pressure control valve or stopcock 280 and extends into the trocar. The pressure control valve 280 is used to control pressure within the patient. The gas pressure control system further has a pressure sensor 282 connected to the tubing 292 to sense pressure in the tubing 292 and a pressure sensor 284 for sensing pressure in the pressure control valve 280. As shown in FIG. 2C, the tubing 292 is actually tube within a tube such that gas supplied from the generator travels to the trocar and patient through tube 296 and gas is released out of the patient through tube 294.

As shown in FIG. 2A the connector 132 to which control module 230 is connected has a gas-enhanced electrosurgical instrument 160 having a connector 162 connected to in. In FIG. 2A, gas control module 230 controls flow of argon gas, so the instrument 160 is an argon gas-enhanced electrosurgical tool such as an argon plasma probe such as is disclosed in U.S. Pat. No. 5,720,745, a hybrid plasma cut accessory such as is disclosed in U.S. Patent Application Publication No. 2017/0312003 or U.S. Patent Application Publication No. 2013/0296846, or a monopolar sealer such as is disclosed in U.S. Patent Application Publication No. 2016/0235462. Other types of argon surgical devices similarly can be used. As shown in FIG. 2B the connector 132 to which control module 240 is connected has a gas-enhanced electrosurgical instrument 170 having a connector 172 connected to in. In FIG. 2B, gas control module 240 controls flow of helium gas, so the instrument 170 is, for example, a cold atmospheric plasma attachment such as is disclosed in U.S. Patent Application Publication No. 2016/0095644.

The system provides for control of intraabdominal pressure in a patient. The pressure control valve 280 has a chamber within it. The pressure in that chamber is measured by pressure sensor 284. $CO_2$ is supplied to the chamber within pressure control valve 280 from gas control module 220 via 3-way proportional valve 260. Pressure in that chamber within the pressure control valve 280 also may be released via 3-way proportional valve 260. In this manner, the system can use the pressure sensor 284 and the 3-way proportional valve to achieve a desired pressure (set through a user interface) in the chamber within the pressure control valve 280. The pressure sensor 282 senses the pressure in the tubing 294 (and hence the intraabdominal pressure). The pressure control valve 280 then releases pressure through its exhaust to synchronize the intraabdominal pressure read by sensor 282 with the pressure in the chamber within the pressure control valve as read by pressure sensor 284. The readings from sensors 282, 284 can be provided to CPU 210, which in turn can control flow of $CO_2$ and one of argon and helium, depending on the procedure being performed, to achieve a stable desired intraabdominal pressure.

Figure 2D:
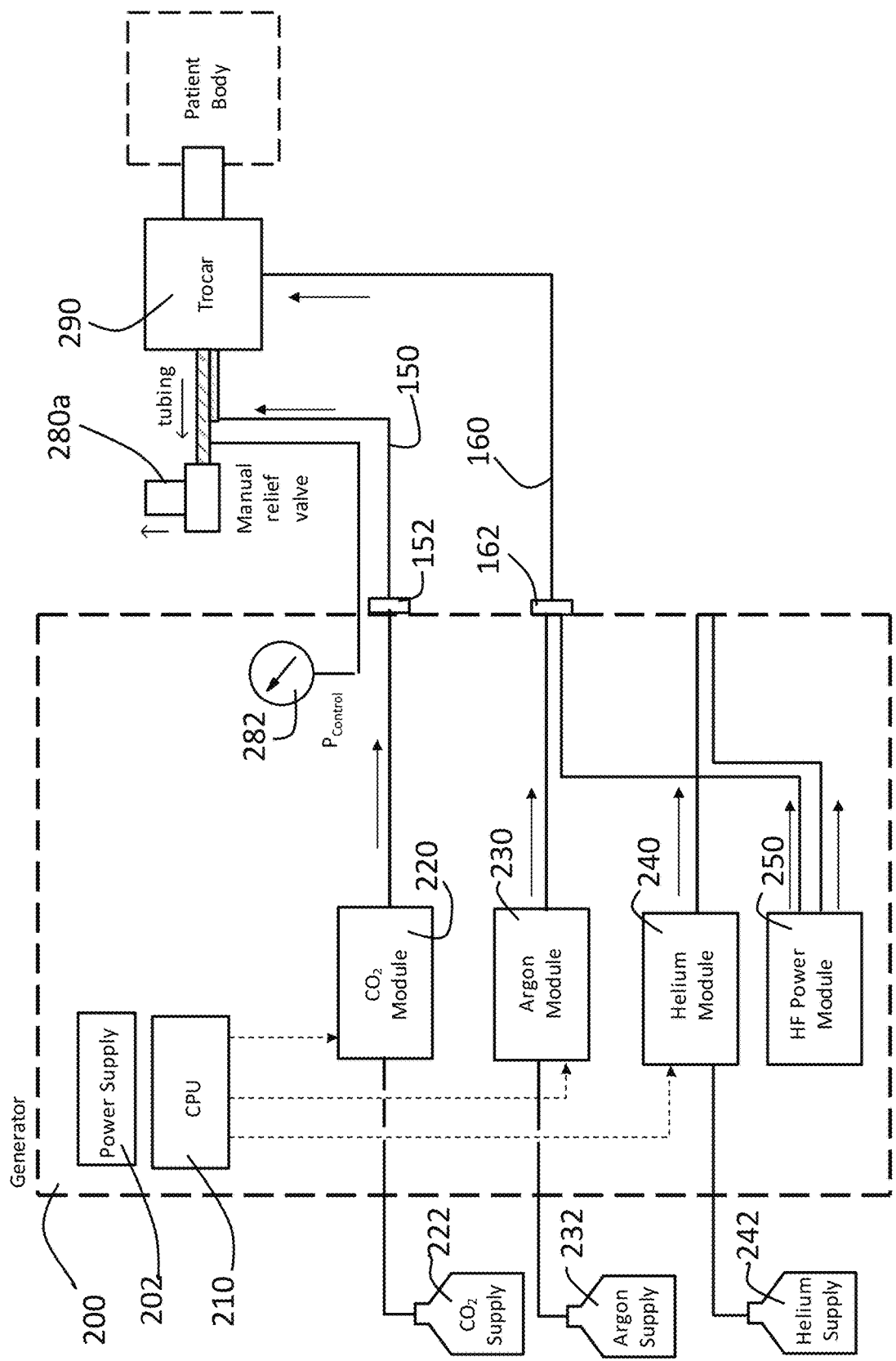
FIG. 2D is a block diagram of an alternate preferred embodiment of pressure control system of a gas-enhanced electrosurgical generator having a pressure control system in accordance with the present invention configured to perform an argon-enhanced electrosurgical procedure.

An alternative embodiment of the gas pressure control system is shown in FIG. 2D. This this system the automatic stopcock or pressure control valve 280 has been replaced by a manual relief valve 280a that is controlled or operated by the surgeon using the system.

A gas control module 300 in accordance with the present invention is designed for gas-enhanced electrosurgical systems. Conventionally, gas-enhanced electrosurgical systems have an electrosurgical generator and a gas control unit that have separate housings. The conventional gas control unit typically controls only a single gas such as argon, $CO_2$ or helium. The present invention is a gas control module 300 that may be used in a gas control unit or in a combined unit functioning both as an electrosurgical generator and as a gas control unit. Further, a plurality of gas control modules in accordance with the present invention may be combined in a single gas control unit or combination generator/gas control unit to provide control of multiple gases and provide control for multiple types of gas-enhanced surgery such as argon gas coagulation, hybrid plasma electrosurgical systems and cold atmospheric plasma systems.

Figure 3A:
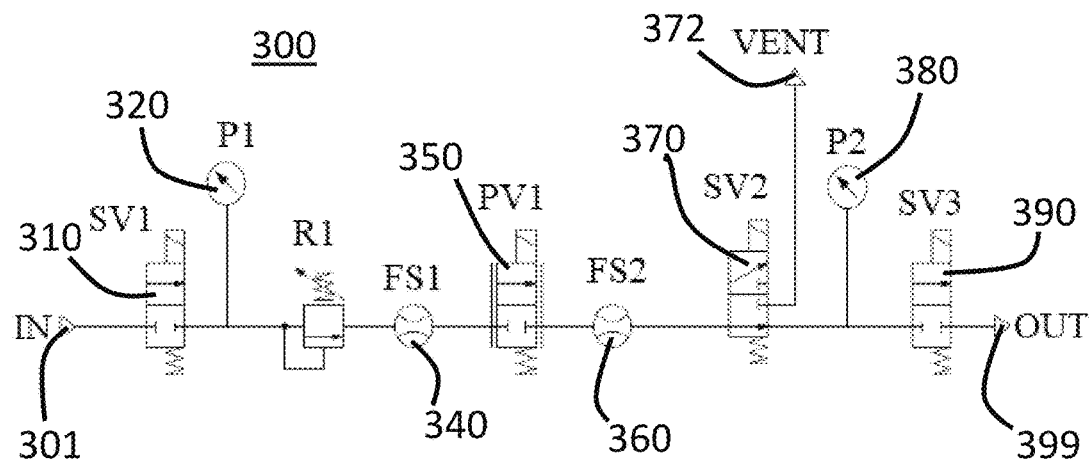
FIG. 3A is a schematic flow diagram illustrating the gas flow through the module and the method by which the module controls the gas flow in accordance with a preferred embodiment of the present invention.

FIG. 3A is a schematic flow diagram illustrating the gas flow through the gas control module 300 and the method by which the module 300 controls the gas flow in accordance with a preferred embodiment of the present invention. As shown in FIG. 3A, the gas enters the gas control module at an inlet port (IN) 301 and proceeds to first solenoid valve (SV1) 310, which is an on/off valve. In an exemplary embodiment, the gas enters the gas module at a pressure of 75 psi. The gas then proceeds to a first pressure sensor (P1) 320, to a first pressure regulator (R1) 330. In an exemplary embodiment, the first pressure regulator (R1) 330 reduces the pressor of the gas from 75 psi to 18 psi. After the pressure regulator (R1) 330, the gas proceeds to flow sensor (FS1) 340, which sense the flow rate of the gas. Next, the gas proceeds to proportional valve (PV1) 350, which permits adjustment of a percentage of the opening in the valve. The gas then proceeds to a second flow sensor (FS2) 360, which senses the flow rate of the gas. This second flow sensor (FS2) 360 provides redundancy and thus provides greater safety and accuracy in the system. Next the gas proceeds to a second solenoid valve (SV2) 370, which is a three-way valve that provides for a vent function that can allow gas to exit the module through a vent 372. The gas then proceeds to a second pressure sensor (P2) 380, which provides a redundant pressure sensing function that against produces greater safety and accuracy of the system. Finally, the gas proceeds to a third solenoid valve (SV3) 390, which is a two-way on/off valve that is normally closed and is the final output valve in the module. The gas exits the module at and output port (OUT) 399, which is connected to tubing or other channel that provides a passageway for the gas to flow to an accessory connected to the electrosurgical unit.

Figure 3B:
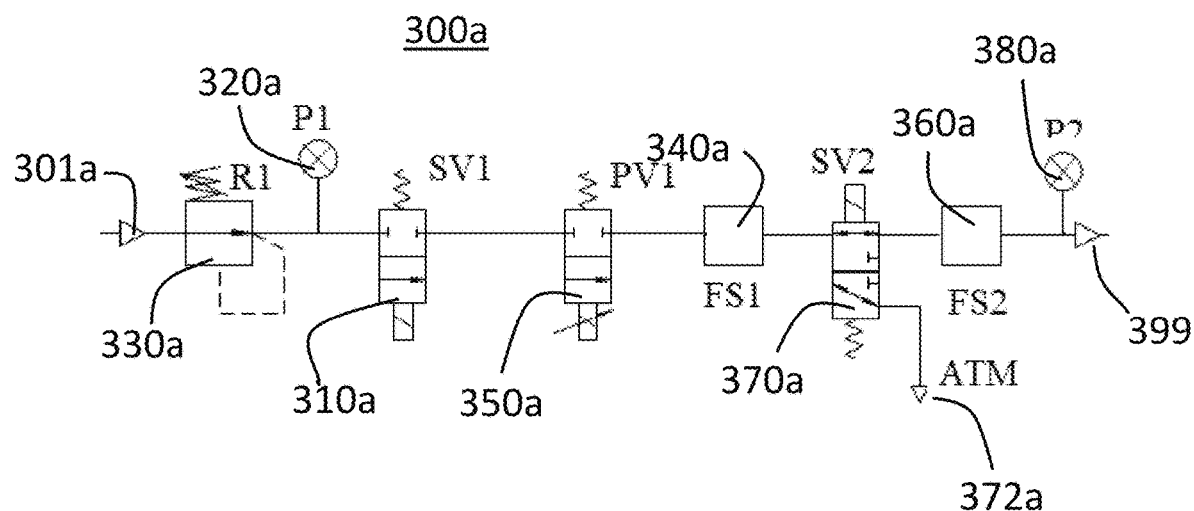
FIG. 3B is a schematic flow diagram illustrating the gas flow through an alternate embodiment of the module and the method by which the module controls the gas flow in accordance with a preferred embodiment of the present invention.

FIG. 3B is a schematic flow diagram of an alternate embodiment of a gas control module illustrating the gas flow through the gas control module 300a and the method by which the module 300a controls the gas flow in accordance with a preferred embodiment of the present invention. As shown in FIG. 3B, the gas enters the gas control module at an inlet port 301a and proceeds to a first pressure regulator (R1) 330a. In an exemplary embodiment, the first pressure regulator (R1) 330a reduces the pressor of the gas from about 50-100 psi to 15-25 psi. After the pressure regulator (R1) 330a, the gas proceeds to a first pressure sensor (P1) 320a and then to a first solenoid valve (SV1) 310a, which is an on/off valve. Next, the gas proceeds to proportional valve (PV1) 350a, which permits adjustment of a percentage of the opening in the valve. Next, the gas proceeds to flow sensor (FS1) 340a, which sense the flow rate of the gas. Next, the gas proceeds to a second solenoid valve (SV2) 370a, which is a three-way valve that provides for a vent function that can allow gas to exit the module through a vent 372a. The gas then proceeds to a second flow sensor (FS2) 360a, which senses the flow rate of the gas. This second flow sensor (FS2) 360a provides redundancy and thus provides greater safety and accuracy in the system. The gas then proceeds to a second pressure sensor (P2) 380a, which provides a redundant pressure sensing function that against produces greater safety and accuracy of the system. The gas exits the module at and output port 399a, which is connected to tubing or other channel that provides a passageway for the gas to flow to an accessory connected to the electrosurgical unit.

The various valves and sensors in either embodiment of the module are electrically connected to a main PCB Board through a connector 490. The PCB connector 490 is connected to a PCB Board that has a microcontroller (such as CPU 210 in the embodiment shown in FIG. 2A). As previously noted, a plurality of gas modules can be in a single gas control unit or single electrosurgical generator to provide control of multiple differing gases. The plurality of gas control modules further may be connected to the same PCB Board, thus providing common control of the modules.

A gas control module of the embodiment of FIG. 3A is shown in further detail in FIGS. 3C-3H. The gas control module has a frame, housing or other support structure 302. The various components forming the gas control modules are connected directly or indirectly to the frame, housing or other support structure 302. The frame, housing or other support member 302 may be formed, for example, from steel, plastic or any other material having sufficient strength to support the components of the module. The frame, housing, or other support member 302 may have a surface for receiving, for example, a manufacturer's label 304 or other identifying information.

Figure 3C:
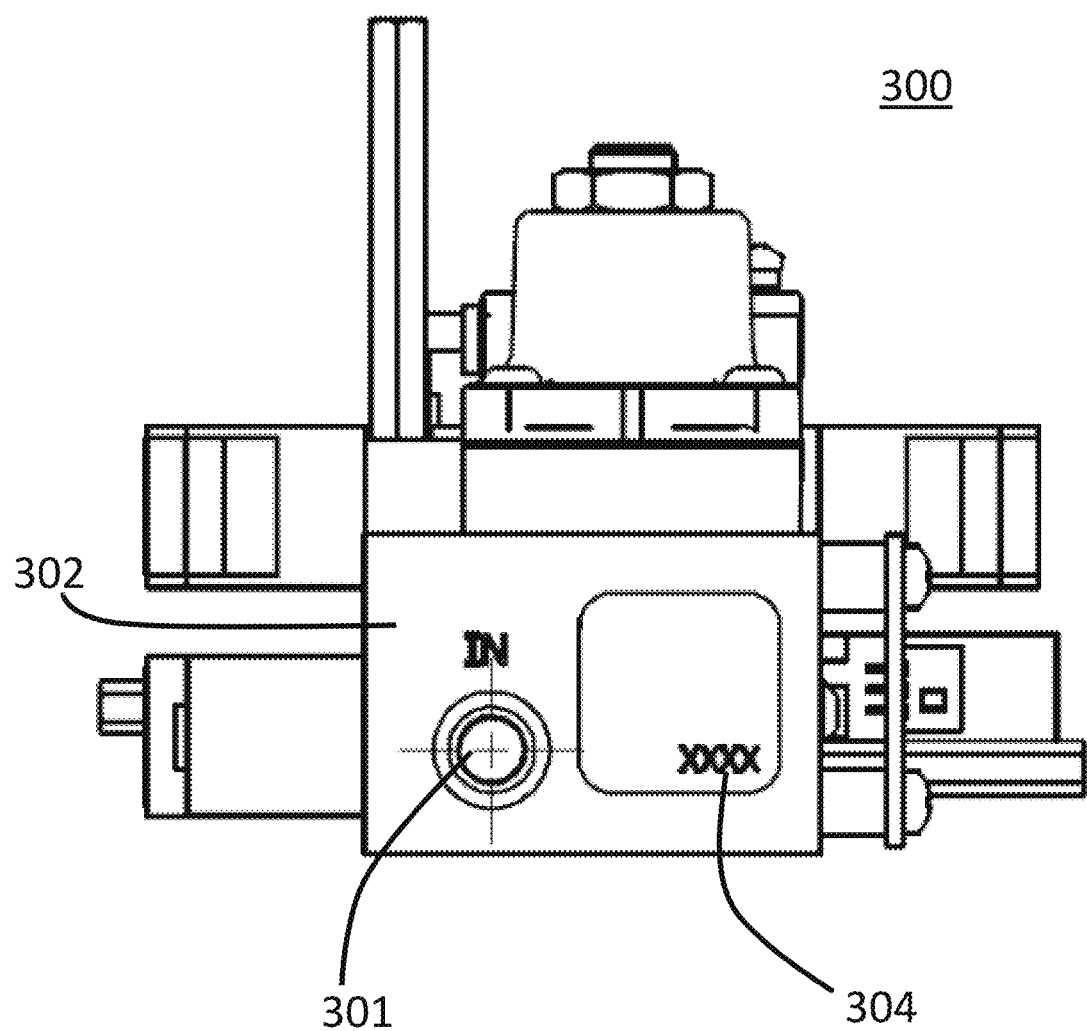
FIG. 3C is a front view of a gas module in accordance with a preferred embodiment of the present invention.
Figure 3D:
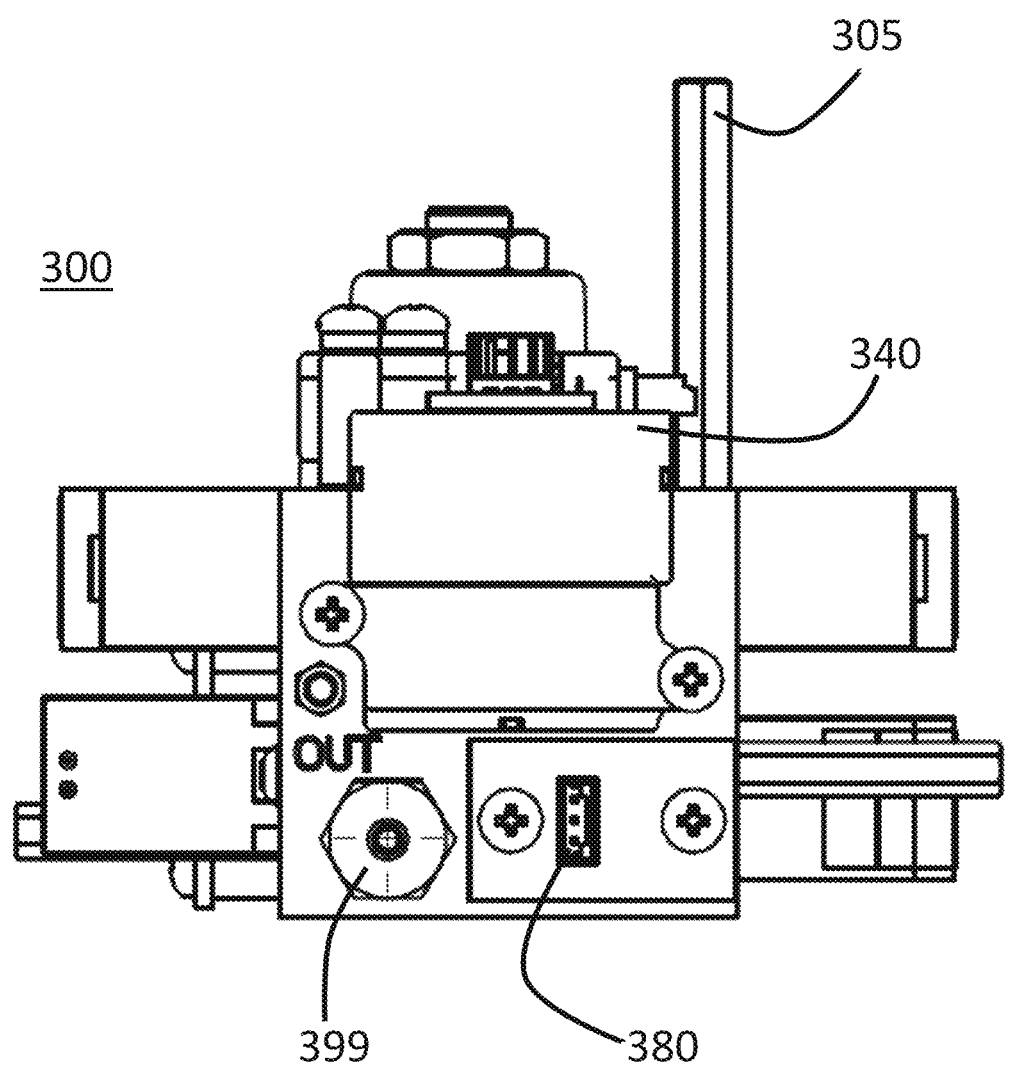
FIG. 3D is a back view of a gas module in accordance with a preferred embodiment of the present invention.
Figure 3E:
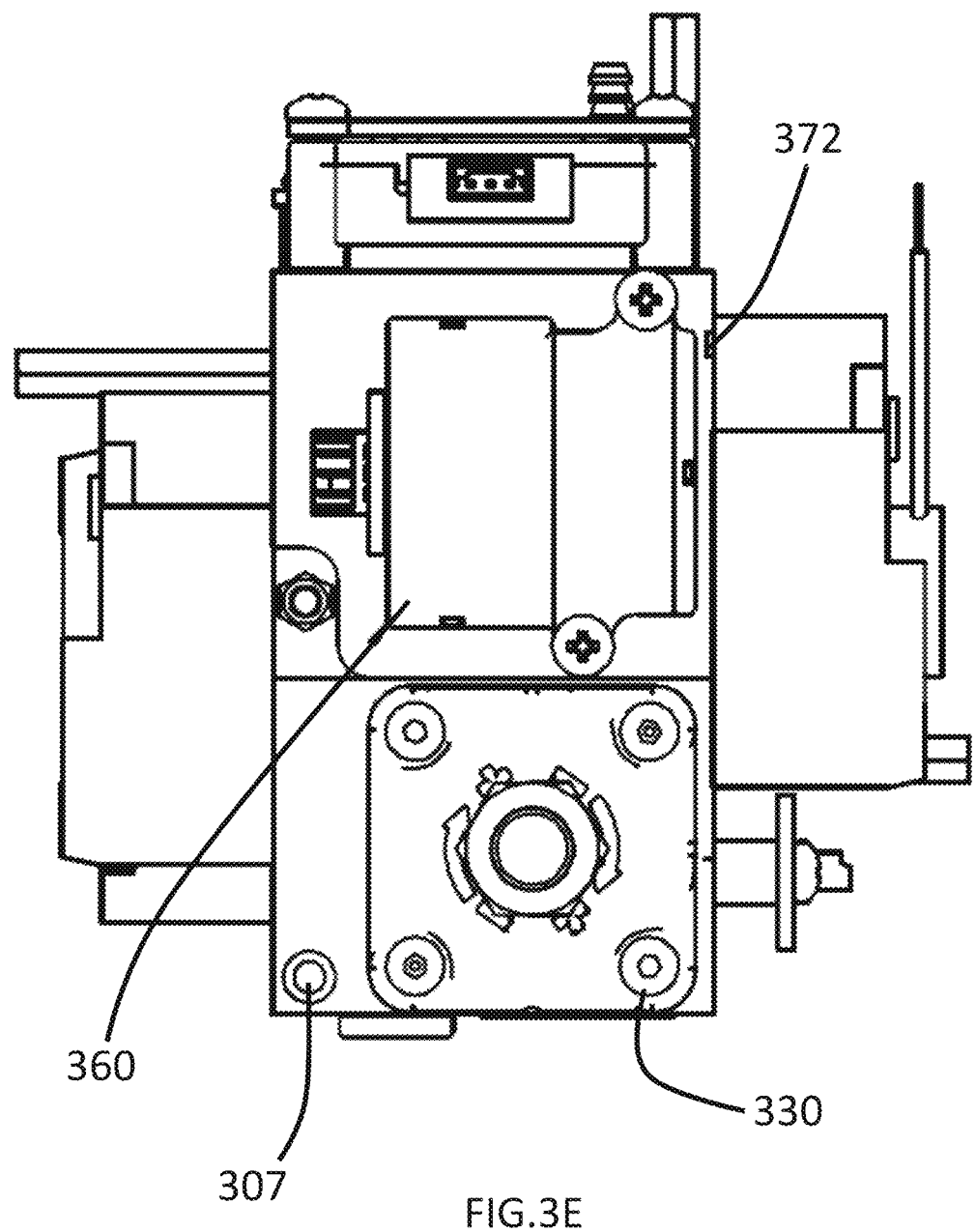
FIG. 3E is a top view of a gas module in accordance with a preferred embodiment of the present invention.
Figure 3F:
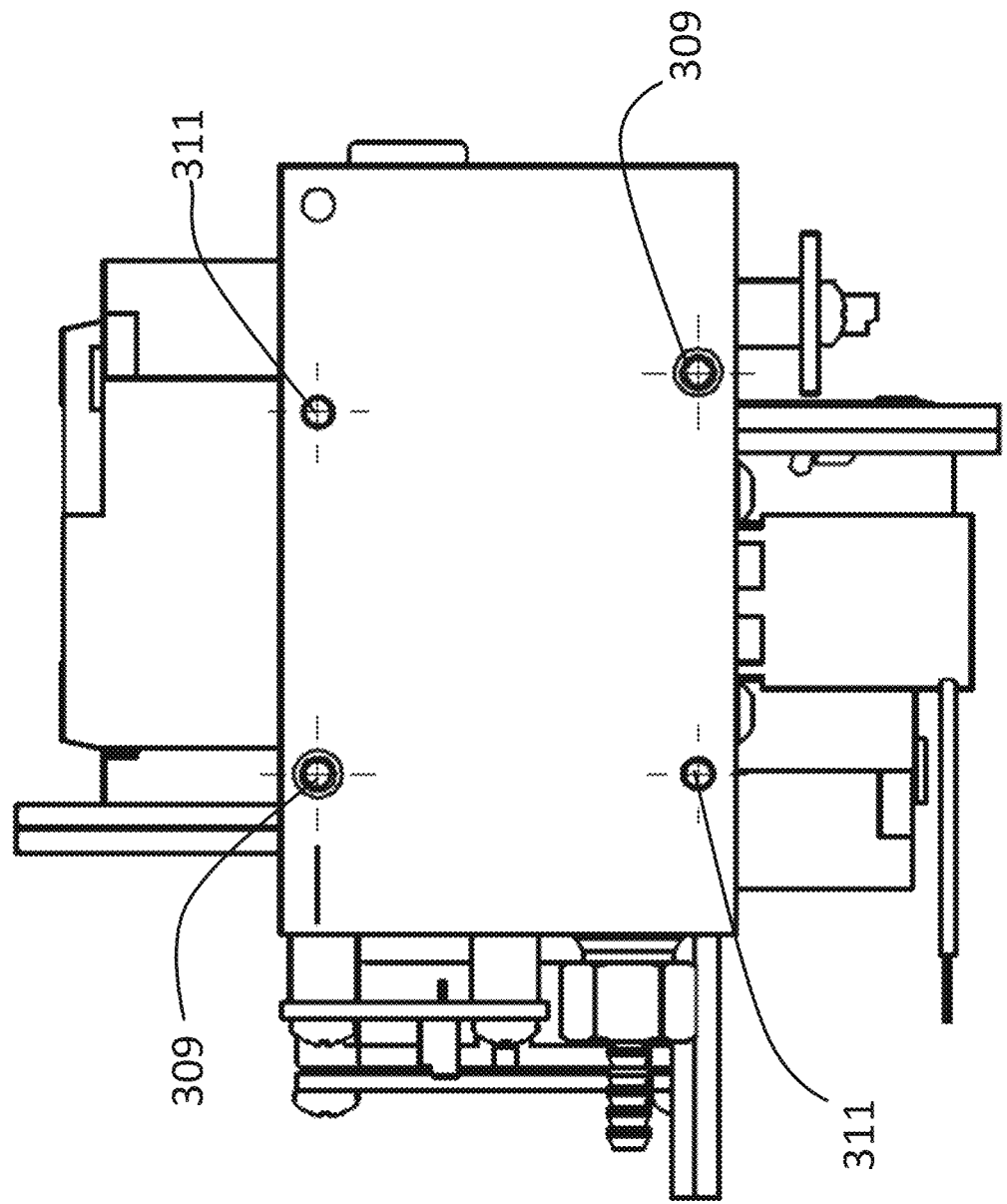
FIG. 3F is a bottom view of a gas module in accordance with a preferred embodiment of the present invention.
Figure 3G:
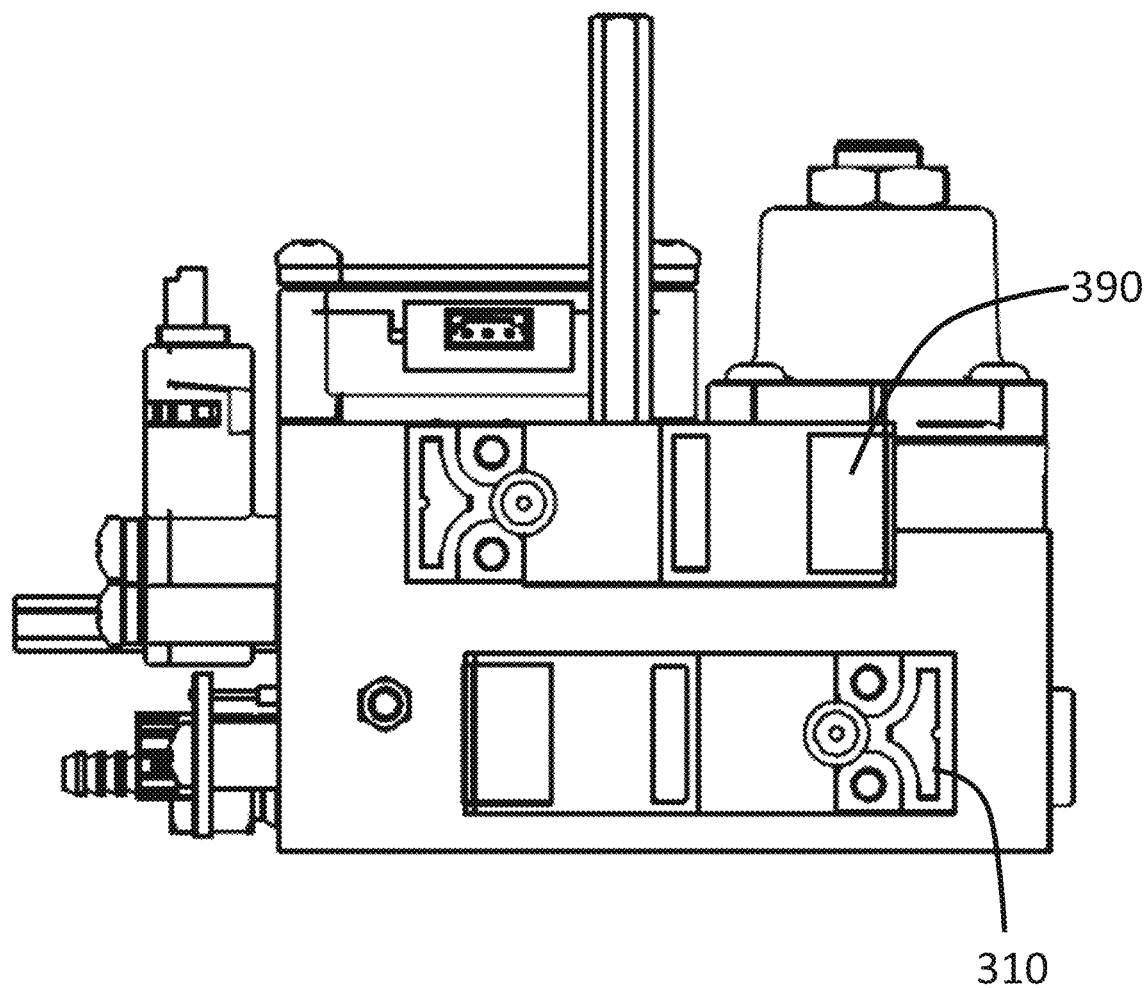
FIG. 3G is a first side view of a gas module in accordance with a preferred embodiment of the present invention.
Figure 3H:
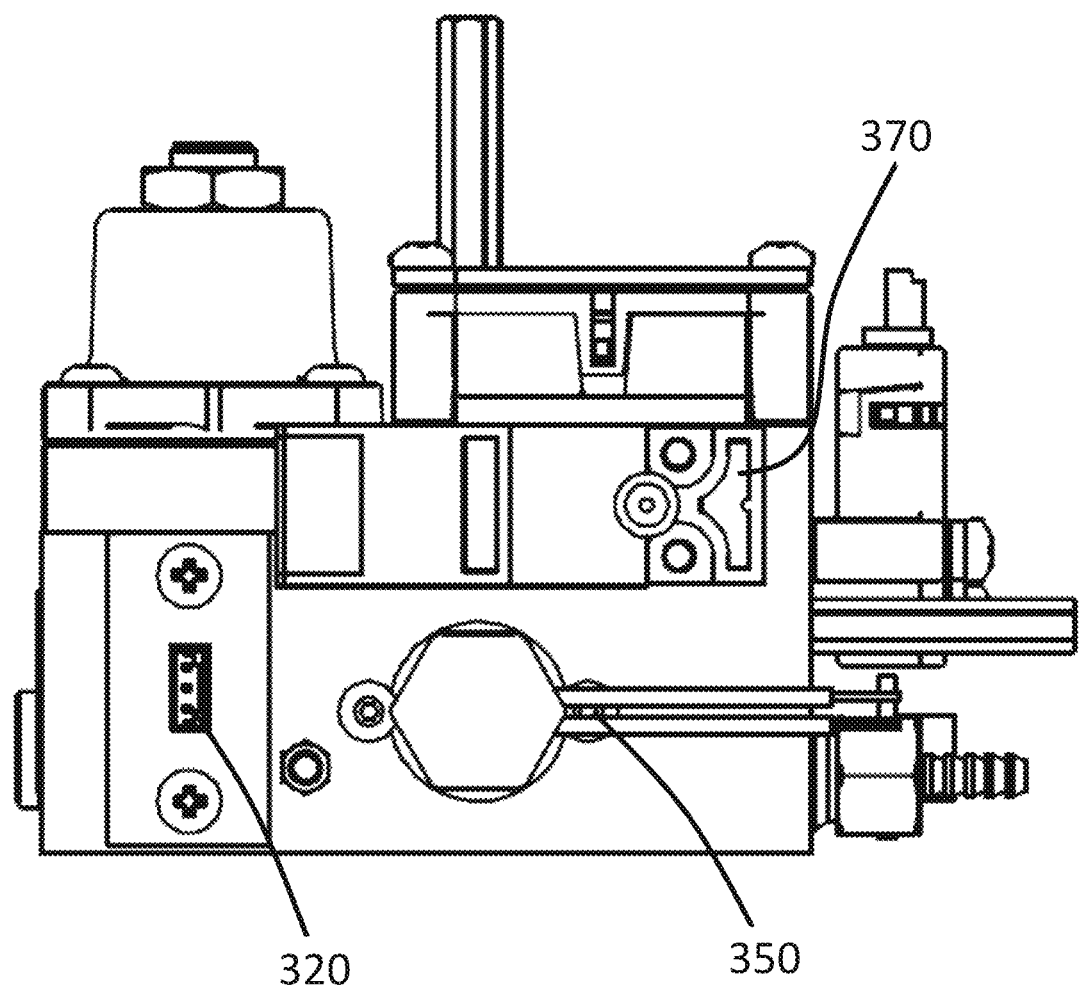
FIG. 3H is a second side view of a gas module in accordance with a preferred embodiment of the present invention.

As shown in FIG. 3C, the gas control module further has an outlet port 399, a mass flow sensor (FS1) 340 and a pressure sensor assembly (P2) 380. The module further may have, for example, a brass standoff 305. As shown in FIG. 3D, the gas control module further has a miniature medical regulator (R1) 330 and a mass flow sensor (FS2) 360. A vent 372 is connected to solenoid valve (SV2) 370. As shown in FIGS. 3C-3H the gas control module has a variety of stackable mounting features 307, 309 and screw holes 311 for mounting the module in a housing. As shown in FIG. 3G, the gas control module further has a solenoid vale (SV1) 310, which is an on/off valve, and a 2-way solenoid valve (SV3) 390. As shown in FIG. 3H, the module further has a solenoid valve (SV2) 370, a pressure sensor assembly (P1) 320 and a proportional valve (PV1) 350.

Figure 4A:
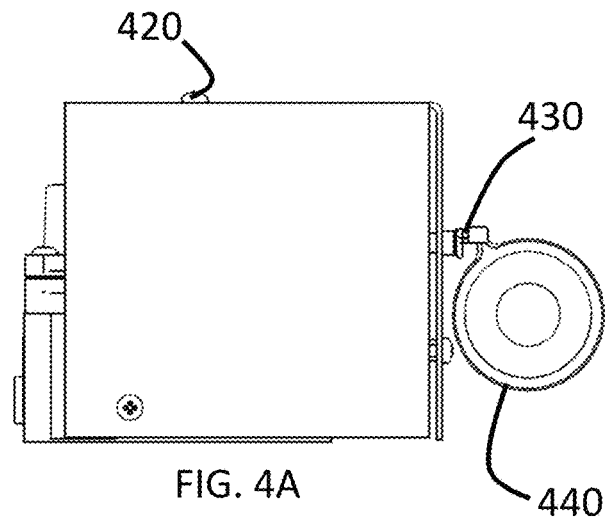
FIG. 4A is a top view of a gas module within a housing or shield in accordance with a preferred embodiment of the present invention.
Figure 4B:
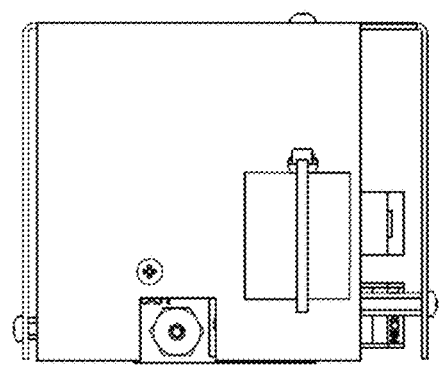
FIG. 4B is a side view of a gas module within a housing or shield in accordance with a preferred embodiment of the present invention.
Figure 4C:
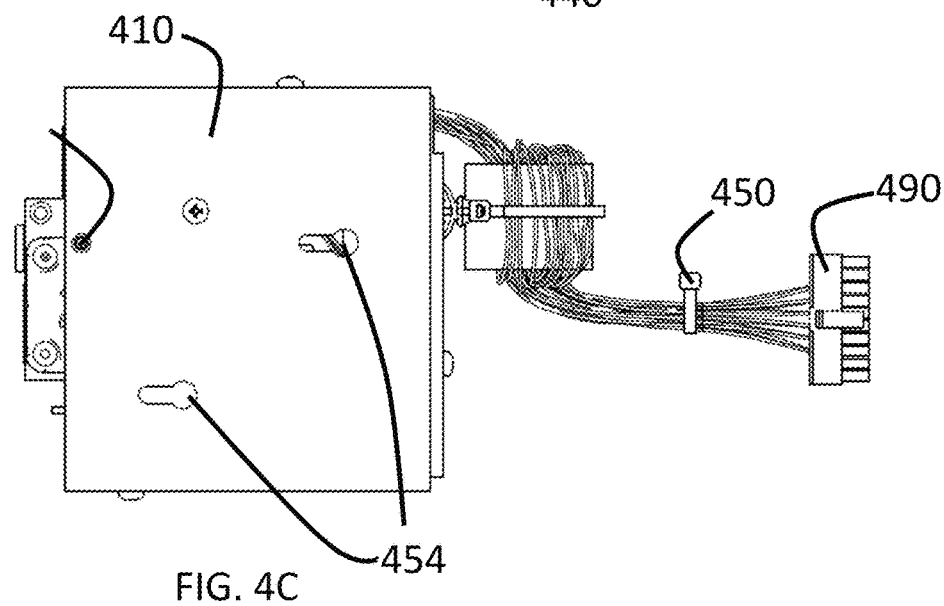
FIG. 4C is a bottom view of a gas module within a housing or shield in accordance with a preferred embodiment of the present invention.

FIGS. 4A-4C show a preferred embodiment of a gas control module with an EMI shield or housing on the module 410. The EMI shielding may be secured to the module, for example, with pan head screws inserted into screw holes 311. The EMI shielding or housing has stackable mounting features 452, 454. The EMI shielding or housing further may have a cable tie in push mount 430 and ferring ring 440 and zip ties 450 for securing wires connected to the various components in the gas control module. The wires are connected to a main PCB connector 490.

All of the features of the housing, frame or other support structure 102, the EMI shielding, the stacking features and mounting features similarly can be incorporated in the embodiment shown in FIG. 3B or in other embodiments of the invention.

Figure 5:
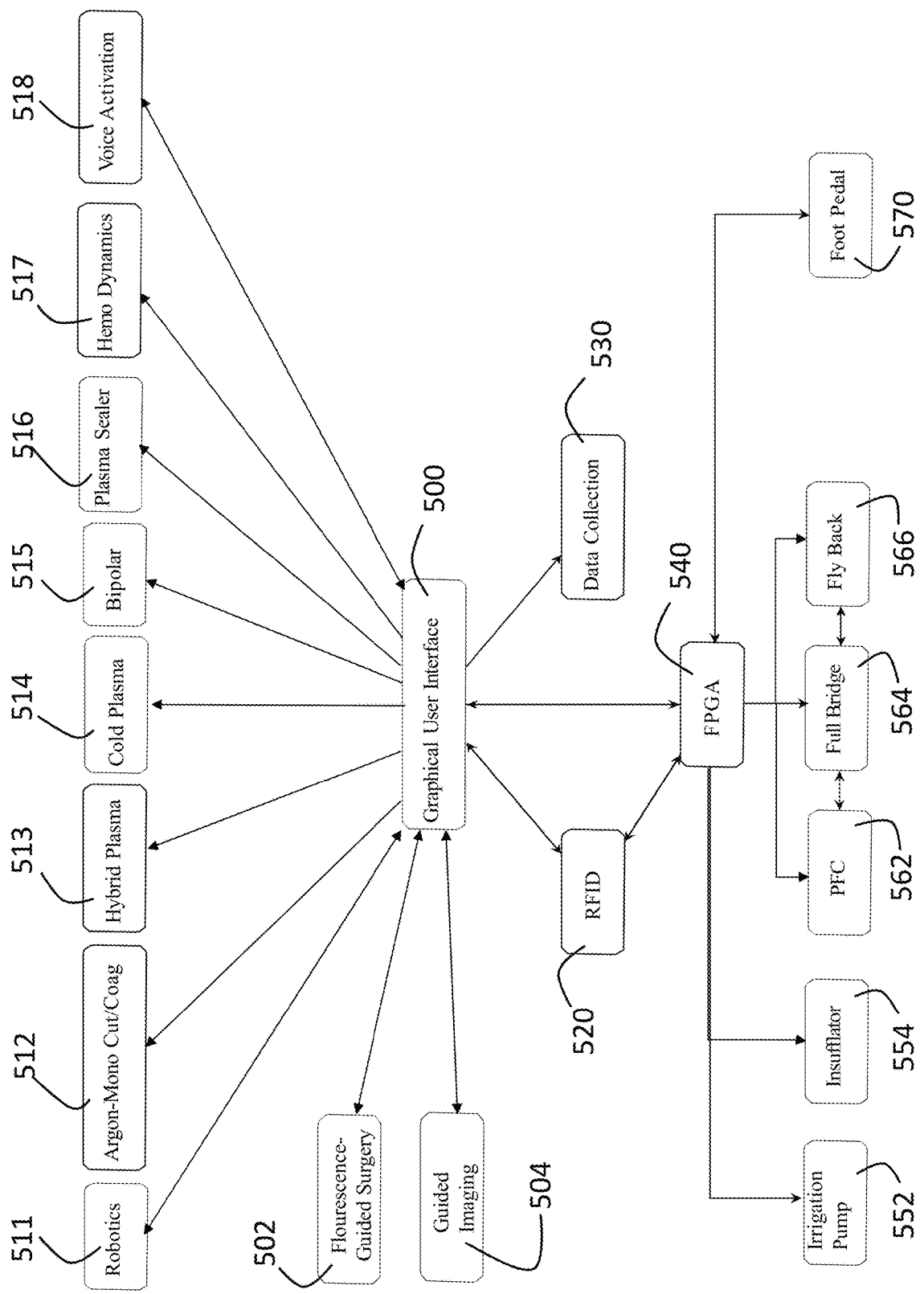
FIG. 5 is a diagram of a graphical user interface in accordance with a preferred embodiment of the present invention.

As shown in FIG. 5, the generator further may have graphical user interface 500 for controlling the components of the system using the touch screen display 120. The graphical user interface 500 for example, may control robotics 511, argon-monopolar cut/coag 512, hybrid plasma cut 513, cold atmospheric plasma 514, bipolar 515, plasma sealer 516, hemo dynamics 517 or voice activation 518. The graphical user interface further may be used with fluorescence-guided surgery 502. For example, J. Elliott, et al., "Review of fluorescence guided surgery visualization and overlay techniques," BIOMEDICAL OPTICS EXPRESS 3765 (2015), outlines five practical suggestions for display orientation, color map, transparency/alpha function, dynamic range compression and color perception check. Another example of a discussion of fluorescence-guided surgery is K. Tipirneni, et al., "Oncologic Procedures Amenable to Fluorescence-guided Surgery," Annals of Surgery, Vo. 266, No. 1, July 2017). The graphical user interface (GUI) further may be used with guided imaging such as CT, MM or ultrasound. The graphical user interface may communicate with RFID 520 (such as may be found in various electrosurgical attachments) and may collect and store usage data 530 in a storage medium. The graphical user interface 500 communicates with FPGA 540, which may control irrigation pump 552, insufflator 554, PFC 562, full bridge 564 for adjusting the power output, fly back 566 for regulating the power (DC to AC) and a foot pedal 570.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:
1. A gas-enhanced electrosurgical generator comprising:
 a housing;
 a first gas control module in said housing and configured to control flow of a first gas, said first gas control module comprising a flow sensor, a pressure sensor, a solenoid valve, and a first frame, wherein said first frame is mounted to said housing;
a second gas control module in said housing and configured to control flow of a second gas, said second gas control module comprising a flow sensor, a pressure sensor a solenoid valve, and a second frame, wherein said second frame is mounted to said housing;
a high frequency power module;
a electronic controller within said housing and configured to control said first gas control module, said second gas control module and said high frequency power module;
a first connector secured on an exterior of said housing, wherein said first connector comprises a fluid connector connected to an output port of said first gas control module; and
a sub-system configured to control intraabdominal pressure in a patient, wherein said sub-system for controlling intraabdominal pressure in a patient comprises:
a 3-way proportional valve connected to an output port of said first gas control module;
a pressure control valve having an internal pressure chamber, a port to said internal pressure chamber, an exhaust and an exterior port configured to release intraabdominal pressure from a patient;
a first pressure sensor for sensing a pressure in said chamber; and
a second pressure sensor connected to said exterior port.

2. The gas-enhanced electrosurgical generator according to claim 1 further comprising:
a second connector secured on an exterior of said housing, wherein said second connector comprises:
a fluid connector connected to an output port of said second gas control module; and
an electrical connector connected to an output of said high frequency power module.

3. The gas-enhanced electrosurgical generator according to claim 2 wherein said first gas comprises $CO_2$ and said second gas comprises argon.

4. The gas-enhanced electrosurgical generator according to claim 3 further comprising a touch-screen display mounted to said housing.

5. The gas-enhanced electrosurgical generator according to claim 2 wherein said first gas comprises $CO_2$ and said second gas comprises helium.

6. The gas-enhanced electrosurgical generator according to claim 5 further comprising a touch-screen display and a graphical user interface, wherein said controller is configured to control said graphical user interface and said touch-screen display.

7. The gas-enhanced electrosurgical generator according to claim 2 further comprising:
a third gas control module in said housing and configured to control flow of a third gas;
a third connector secured on an exterior of said housing, wherein said third connector comprises:
a fluid connector connected to an output port of said third gas control module; and
an electrical connector connected to an output of said high frequency power module.

8. The gas-enhanced electrosurgical generator according to claim 7 wherein said first gas comprises $CO_2$, said second gas comprises argon and said third gas comprises helium.

9. A gas-enhanced electrosurgical generator comprising:
a housing;
a first gas control module in said housing and configured to control flow of a first gas;
a second gas control module in said housing and configured to control flow of a second gas;
a high frequency power module; and
a controller within said housing and configured to control said first gas control module, said second gas control module and said high frequency power module; and
a sub-system configured to control intraabdominal pressure in a patient, wherein said sub-system for controlling intraabdominal pressure in a patient comprises:
a 3-way proportional valve connected to an output port of said first gas control module;
a pressure control valve having an internal pressure chamber, a port to said internal pressure chamber, an exhaust and an exterior port configured to release intraabdominal pressure from a patient;
a first pressure sensor for sensing a pressure in said chamber; and
a second pressure sensor connected to said exterior port.

10. A gas-enhanced electrosurgical generator comprising:
a housing;
a first gas control module in said housing and configured to control flow of a first gas, said first gas control module comprising a flow sensor and a pressure sensor;
a second gas control module in said housing and configured to control flow of a second gas, said first gas control module comprising a flow sensor and a pressure sensor;
a high frequency power supply;
an electronic controller within said housing and configured to control said first gas control module, said second gas control module and said high frequency power module; and
a sub-system configured to control intraabdominal pressure in a patient, wherein said sub-system for controlling intraabdominal pressure in a patient comprises:
a 3-way proportional valve connected to an output port of said first gas control module;
a pressure control valve having an internal pressure chamber, a port to said internal pressure chamber, an exhaust and an exterior port configured to release intraabdominal pressure from a patient;
a first pressure sensor for sensing a pressure in said chamber; and
a second pressure sensor connected to said exterior port;
wherein said high frequency power supply is configured to supply high frequency energy to an argon plasma coagulation attachment and supply low frequency electrosurgical energy to a cold atmospheric plasma attachment based upon settings input through said touch screen.

11. The gas-enhanced electrosurgical generator according to claim 10, wherein said first gas control module further comprises a plurality of flow sensors, a plurality of pressure sensors, and a solenoid valve.

* * * * *